United States Patent [19]

Ohmoto et al.

[11] Patent Number: 5,360,716
[45] Date of Patent: Nov. 1, 1994

[54] HUMAN TUMOR NECROSIS FACTOR αSPECIFIC MONOCLONAL ANTIBODY AND METHOD FOR DETECTING HUMAN TUMOR NECROSIS FACTOR α

[75] Inventors: Yasukazu Ohmoto, Itano; Tsutomu Nishida, Naruto; Keiko Mizuno, Tokushima; Satoru Nakai, Itano, all of Japan

[73] Assignee: Otsuka Pharmaceutical Co., Ltd., Tokyo, Japan

[21] Appl. No.: 22,428

[22] Filed: Feb. 16, 1993

Related U.S. Application Data

[63] Continuation of Ser. No. 759,976, Sep. 17, 1991, abandoned, which is a continuation of Ser. No. 427,277, Oct. 24, 1989, abandoned.

[30] Foreign Application Priority Data

Oct. 24, 1988 [JP] Japan .................. 63-267897

[51] Int. Cl.$^5$ ............... G01N 33/53; C12N 5/18; C07K 15/28
[52] U.S. Cl. .................. 435/7.2; 435/240.27; 435/70.21; 435/172.2; 530/388.23
[58] Field of Search ............ 530/388.23; 435/240.27, 435/172.2, 70.21, 7.2

[56] References Cited

FOREIGN PATENT DOCUMENTS 0218868 8/1986 European Pat. Off. .

OTHER PUBLICATIONS

Hahn et al. PNAS 82: 3814 1985.
Kipps et al. pp. 108.1–108.9 in Weir et al., eds. Adv. Exptl. Immunol. vol. 4 Blackwell Sci Publ. 1986.
Wang et al. Science 228: 149, 1985.
Pennica et al. Nature 312:724, 1984.
Bringman et al. Hybridoma 6: 489–507, 1987.
Fendly et al. Hybridoma 6: 359, 1987.
Hayashi et al. pp. 820–1 in Recent Adv. Chemother. Proc. Int'l. Congr. Chemother, 14th vol., Ishigami ed. Univ. Tokyo Press, 1985.
Liang et al. Biochem Biophysres Comm 137:847 1986.
Prince et al. J. Pharmaceutical and Biomedical Analysis 5:793–802, 1987.
Aggrawal et al. J. Biol. Chem. 260:2345, 1985.
Pennica et al. PNAS 82:6060, 1985.
Beutler et al. Science 229: 869, 1985.
Gamble et al. PNAS 82: 8667 1985.
Urban et al. PNAS 83:5233, 1986.

*Primary Examiner*—Paula R. Hutzell
*Attorney, Agent, or Firm*—Sughrue, Mion, Zinn, Macpeak & Seas

[57] ABSTRACT

Monoclonal antibodies exhibiting specificity for human TNF-α are disclosed. The antibodies are useful for immunological purification and for measurement of said human TNF-α in immunoassays.

3 Claims, No Drawings

HUMAN TUMOR NECROSIS FACTOR αSPECIFIC MONOCLONAL ANTIBODY AND METHOD FOR DETECTING HUMAN TUMOR NECROSIS FACTOR α

This is a continuation of application No. 07/759,976 filed Sep. 17, 1991, now abandoned, which is a continuation of application No. 07/427,277 filed Oct. 24, 1989, now abandoned.

BACKGROUND OF THE INVENTION

1. Field of the Invention

The present invention relates to monoclonal antibodies for human TNFs (tumor necrosis factors), and, more particularly, to monoclonal antibodies for a human TNF which are useful as a medicine and ensure immunological purification and measurement of said human TNF.

2. Description of the Background Art

A lipopolysaccharide (LPS), when administered to a mouse, rabbit, or rat sensitized by *Bacillus de Calmette Guerin* (BCG), induces a serum factor which hemorrhagically necroses tumors. Carswell et al. named this factor "TNF" in 1975 [*Proc. Nat. Acad. Sci.*, USA, 72. 3666 (1975)]. Macrophages proliferate in the spleen of a mouse sensitized with BCG but elapse by the administration of LPS. From this, TNF has been considered to be produced by macrophages. Recent studies have unveiled the fact that an in vitro LPS treatment of isolated macrophages induced a TNF activity in the supernatant of the macrophage culture broth, confirming that macrophages are TNF-producing cells. Several leukemia cells producing TNF have also been reported.

The characteristic of TNF destroying various cancer cells and inhibiting their growth, while exhibiting no such effects on normal cells, suggests its potential utility as a carcinostatic agent. The anti-tumor activity of TNF has been confirmed in experiments using a purified TNF derived from mice and rabbits.

The TNF activity has been measured using a fibroblast cell line, L929, having a strong sensitivity to a TNF. The TNF unit of activity is generally expressed as the amount which results in a 50% cytotoxicity of L929 cells in a culture plate.

The molecular weights of TNF produced by various animals as determined by a gel filtration analysis are reported to be 150,000 and 40,000–60,000 for TNF produced by mouse, 67,000 and 39,000 for TNF produced by rabbit, and 34,000–140,000 for TNF produced by human. According to molecular weight determination using SDS-PAGE, purified TNFs derived from rabbit and human are reported to be 17,000. TNFs having this molecular weight are termed "TNF-α" or tumor necrosis factor-alpha. Natural TNFs are considered to exist as oligomers.

In 1984, the cloning of TNF-cDNA was successfully achieved using human myeloma leukemia cells "HL-60" which are a type of TNF-producing cell. This has ensured large-scale production of TNF using *E. coli*. The cDNA cloning revealed the fact that human TNF is constituted by 157 amino acids and has a long preceding polypeptide having 76 amino acids [D. Pennica et al., Nature, 312, 724–729 (1984)]. Very closely following this, the successful cloning of TNF chromosomal genes was also reported [T. Shirai et al., Nature, 313, 803–806 (1985)], and it was revealed that human TNF genes are composed of four exons.

The amino acid sequence of TNF and the gene base sequence have respectively 28% and 46% homologies with a cytotoxin factor and a lymphotoxin (LT) produced by B-cells. TNF, however, has a substantive difference from LT in that the former has no N-glycosil-type sugar chain bonding site. Although TNF and LT have no immunological cross-reactivity, they exhibit very similar cytotoxicity. The homological portions of TNF and LT are considered to be involved in the cytotoxicity.

As mentioned above, because of its special physiological activity, the utility of TNF as a medicine can be expected. A number of studies have been undertaken with a view to utilize TNF as a medicine. Also, extensive research is are underway on the subject of various immunodeficiencies and immunoreactions, as well as on the subject of TNF assay in clinical samples of diseases related to immunodeficiencies and immunoreactions.

A bioassay technique is currently used for the analysis of the aforementioned TNF-α. According to this method TNF is measured in terms of its activity. The method, however, has problems in its complicated procedure and insufficient accuracy. The method also requires stringent precaution concerning any components interfering with the assay result. Development of a measurement technique substituting for the bioassay technique has therefore been sought.

SUMMARY OF THE INVENTION

Accordingly, an object of the present invention is to provide monoclonal antibodies exhibiting specific reactivities to human TNF-α which are useful as a medicine and ensure immunological purification and measurement of said human TNF.

Other objects, features and advantages of the invention will hereinafter become more readily apparent from the following description.

DETAILED DESCRIPTION OF THE INVENTION AND PREFERRED EMBODIMENTS

According to the present invention monoclonal antibodies having a specificity for human TNF-α is provided.

A novel and simple immunoassay technique for measuring said human TNF-α with high sensitivity and with high precision can be provided by the use of the monoclonal antibodies of the present invention.

Since the monoclonal antibodies of the present invention are specific with respect to TNF-α, they can be utilized for a specific purification of TNF-α if applied to affinity chromatography or the like.

The antibodies of the present invention are hereinafter described in detail.

The antibodies of the present invention can be prepared by using a TNF-α as an antigen. More specifically, a hybridoma is first prepared from mammal phlogocytes (immunocytes) sensitized with said antigen and mammal plasmacytoma cells. A clone capable of producing a desired antibody is selected from the hybridoma, cultured, and collected.

There are no specific limitations as to the types of TNF-α used as an antigen in this method. A supernatant of a culture medium containing a human TNF induced by the application of a known in vitro method or its purified product [*Proc. Natl. Acad. Sci.*, USA, 82, 6637 (1985)], a human TNF produced by the use of a gene recombinant technique [*Nature*, 312, 724–729 (1984)], or a synthetic peptide prepared having a part of the amino acid sequence of one of these TNFs can be used.

There are no specific limitations as to mammals to be immunized with the antigen. It is desirable, however, that the mammal be selected taking into consideration its compatibility with plasmacytoma cells used for the cell fusion. Usually, the use of mouse or rat is advantageous.

Immunization can be performed by administering said antigen to a mammal by intravenous, subcutaneous, intradermic, or intraperitoneal injection. More specifically, the antigen, if desired, mixed with a conventional adjuvant, is administered to an animal, e.g. mouse, once a day at 3–5 intervals until the total amount administered becomes about 100–500 µg/mouse. Preferably immune spleen cells are extracted about 3 days after the above final administration.

There are several cells known in the art as plasmacytoma cells of mammals which can be used as the parent cells to be fused with the immune cells. They are, for example, myeloma tumor cells such as p3 (p3/×63-Ag8) [Nature, 256, 495–497 (1975)], p3-U1 [*Current Topics in Microbiology and Immunology*, 81, 1–7 (1978)], NS-1 [Eur. I. Immunol., 6, 511–519 (1976)], MPC-11 [Cell, 8, 405–415 (1976)], SP2/O [Nature, 276 269–270 (1978)], FO [J. Immunol. Meth., 35, 1–21 (9180)], ×63.6.5.3. [J. Immunol., 123, 1548–1550 (9179)], S194 [J. Exp. Med., 148, 313–323 (1978)], etc., rat R210 [Nature, 277, 131–133 (1979)], and the like.

Fusion of these plasmacytoma cells and the above immune cells can be carried out according to a known method, for example, according to the method of Milstein [*Method in Enzymology*, 73, 3 (1981)]. Specifically, the cell fusion can be carried out in a normal culture medium in the presence of a conventional cell fusion promoter such as polyethylene glycol (PEG), *Sendai virus* (HVJ), etc. An auxiliary agent such as dimethylsulfoxide may be added to the culture medium, if necessary, for further promoting the cell fusion efficiency. The ratio of plasmacytoma cells and immune cells used may be a ratio commonly employed in the art. Usually, immune cells are used in an amount of 1–10 times plasmacytoma cells. Various media commonly used for culturing plasmacytoma cells, RPMI-1640, MEM etc., can be used for the cell fusion. It is desirable that serum adjuncts such as fetal cattle serum (FCS) be eliminated from the medium. The cell fusion is carried out by thoroughly mixing a prescribed amount of plasmacytoma cells and immune cells in a medium and by adding to it about 30–60 w/v% of a PEG solution having an average molecular weight of 1,000–6,000 which is heated in advance to about 37° C. Thereafter, the addition of a suitable medium and centrifugation to remove the supernatant are repeated until a desired hybridoma is formed.

Separation of the hybridoma can be carried out by culturing the hydbridoma in a conventional selection medium, such as, for example, HAT medium (a medium containing hypoxanthine, aminopterin, and thymidine). The culture is carried out for a period of time, usually several days to several weeks, sufficient to destroy cells other than target hybridoma such as unfused cells and the like. The hybridoma thus produced is subjected to screening of the target antibody by means of a conventional limiting dilution analysis and to monocloning.

The screening of the target antibody can be carried out by any one of various methods commonly used for antibody screening, such as the ELISA method [*Engvall, E., Meth. Enzymol.*, 70, 419–439 (9180)], the plaque method, the spot method, the agglutination reaction method, the Ouchterlony method, the radioimmunoassay (RIA) method, and the like ["Hybridoma and Monoclonal Antibody", R&D Planning Publishing Co., 30–53 (1982)]. The above-mentioned antigen can be used for the screening.

The hybridoma thus obtained capable of producing desired monoclonal antibodies which can identify human TNF-α can be subcultured in a normal medium and can be stored in liquid nitrogen for a long period of time.

Collection of desired antibodies from the hybridoma can be performed, for example, by culturing the hybridoma according to a conventional method and collecting the supernatant containing antibodies, or by administering the hybridoma to a mammal having compatibility therewith, allowing the hybridoma to grow, and collecting the antibodies from the abdominal dropsy. The former method is suitable for preparing a high-purity antibody and the latter can be applied to a large-scale production of antibodies.

The antibodies thus produced can be purified by a conventional method such as salting-out, gel permeation, affinity chromatography, or the like.

The monoclonal antibodies of the present invention thus prepared have a specificity for TNF-α.

Among the antibodies of the present invention, there is one type having a neutralizing effect on human TNF-α biological activity. This type of antibody is particularly suitable for the specific measurement of human TNF-α having a biological activity. Also, among the antibodies of the present invention, there is a type which is capable of recognizing specifically different sites of TNF-α, exhibits no steric hindrance between themselves, and, at the same time, can combine with TNF-α. Such an antibody is useful in a sandwich assay and the like. In addition, there are antibodies of the present invention which exhibit a particularly superior reactivity in liquid-phase or solid-phase systems. This type of antibody is suitable for use in liquid- or solid-phase immunoassay.

According to the present invention monoclonal antibodies which have a specificity to human TNF-α are provided. Also, an immunoassay technique having extremely high sensitivity and superior specificity can be provided by the use of antibodies of the present invention. The immunoassay technique can detect and measure with a very high precision human TNF-α in samples such as clinical samples containing even an extremely small amount of human TNF-α.

Other features of the invention will become apparent in the course of the following description of the exemplary embodiments which are given for illustration of the invention and are not intended to be limiting thereof.

EXAMPLES

Example 1

Preparation of Antibodies of the Present Invention

A human TNF-α (10–20 [g) prepared by a gene recombinant technique [*Nature*, 312, 724–729 (1984)] was intraperitoneally administered to a BALB/c mouse together with complete Freund's adjuvant. The same amount of antigen was administered twice together with incomplete Freund's adjuvant, first 3–4 weeks after the initial administration and then 3–4 weeks thereafter. After 3-4 days following the last administration, cell fusion was performed according to a conventional method [*Method in Enzymology*, 73, 3 (1981)], using immunized spleen cells and myeloma tumor cells [P3U1, *Current Topics in Microbiology*, 81, 1-7 (1978)] at a ratio of 10:1 in polyethylene glycol (PEG-4000). The hybridoma was screened with HAT medium. The supernatant was tested by an enzymatic immunoassay technique using a 96-well microplate coated with said human TNF-α and a (goat) peroxidase-labeled anti-mouse IgG (product of E. Y. Laboratories, Inc.), thereby detecting cells capable of producing the target antibody for the human TNF-α.

Cloning by a limiting dilution technique was repeated to produce 7 clones capable of producing the desired antibodies. They were named KOCO701, KOCO702, KOCO703, KOCO704, KOCO705, KOCO706, and KOCO707. The antibodies produced by them were respectively named ANOC701, ANOC702, ANOC703, ANOC704, ANOC705, ANOC706, and ANOC707.

One of the clones, "KOCO 705", was deposited on Jun. 1, 1988 at the Fermentation Research Institute 1-3, Higashi, 1 chome, Tsukuba-shi, Ibaraki-ken 305, Japan under the name of KOCO 705 (FERM BP-2569).

Characteristics of the antibodies produced by each of the above clones are as follows:

(1) Antibody Subclass

The subclass was determined using a mouse antibody subclass detection kit (product of Bio-Rad Co.). The results are given in Table 1.

TABLE 1

| Antibody No. | Subclass |
|---|---|
| ANOC701 | $IgG_1$ |
| ANOC702 | $IgG_1$ |
| ANOC703 | $IgG_{2a}$ |
| ANOC704 | $IgG_1$ |
| ANOC705 | $IgG_1$ |
| ANOC706 | $IgG_1$ |
| ANOC707 | $IgG_1$ |

(2) Antibody Production Level

IgG in ascites was purified using the Protein A affinity, and concentration (mg/ml) was determined by $OD_{280}$ adsorption. The $OD_{280}$ value at a 1 mg/ml IgG concentration was assumed to be 1.4.

The results are shown in Table 2.

TABLE 2

| Antibody No. | IgG (mg/ml) |
|---|---|
| ANOC701 | 0.1 |
| ANOC702 | 1.6 |
| ANOC703 | 0.2 |
| ANOC704 | 1.2 |
| ANOC705 | 1.1 |
| ANOC706 | 8.6 |
| ANOC707 | 2.0 |

(3) Neutralization Antibody Titer

The neutralization antibody titer of the ascites was determined by the LM assay technique which is a type of TNF bioassay. The neutralization antibody titer is defined as the number of a TNF-α units which can be neutralized by 1 ml of ascites.

The results are shown in Table 3.

TABLE 3

| Antibody No. | Neutralization Antibody Titer (U) |
|---|---|
| ANOC701 | 32,000 < |
| ANOC702 | 32,000 < |
| ANOC703 | 2,000 > |
| ANOC704 | 32,000 < |
| ANOC705 | 32,000 < |
| ANOC706 | 32,000 < |
| ANOC707 | 32,000 < |

(4) Molecular Weight

Antibodies obtained from ascites were purified using an IgG purification kit (MOPS Kit, product of Bio-rad Co.). The IgG's heavy-chain and light-chain molecular weights were determined by electrophoresis using SDS-PAGE in the presence of 2 ME. The sum of the two molecular weights was taken as representing one-half of the molecular weight of the intact monoclonal antibodies.

The results are shown in Table 4.

TABLE 4

| Antibody No. | Molecular Weight | | |
|---|---|---|---|
| | Heavy chain | Light chain | IgG |
| ANOC701 | N.T. | N.T. | N.T. |
| ANOC702 | 53.0 | 25.0 | 156 |
| ANOC703 | 53.0 | 24.5 | 155 |
| ANOC704 | 52.0 | 24.0 | 152 |
| ANOC705 | 53.0 | 24.5 | 155 |
| ANOC706 | 53.0 | 23.0 | 152 |
| ANOC707 | 50.0 | 24.0 | 148 |

(5) Western Blotting Analysis

Specificity for TNF-α and non-reactivity with *E. coli* of the antibodies of the present invention were confirmed in the following manner. rTNF-α and rTNF-α-producing *E. coli* were treated with an SDS lysis buffer to a final concentration of 100 μg/ml. SDS-PAGE was performed to effect blotting onto nitrocellulose and to determine the reactivity of each monoclonal antibody.

The results are shown in Table 5.

TABLE 5

| Antibody No. | Reactivity | |
|---|---|---|
| | *E. coli* protein | TNF-α |
| ANOC701 | − | ++ |
| ANOC702 | − | ++++ |
| ANOC703 | − | − |
| ANOC704 | − | ++++ |
| ANOC705 | − | ++ |
| ANOC706 | − | ++ |
| ANOC707 | − | ++ |

Table 5 shows that ANOC701, ANOC702, ANOC704, ANOC705, ANOC706, and ANOC707 combine with TNF-α with specificity and do not react with *E. coli* protein. The non-reactivity of ANOC703 with rTNF-α suggests its recognition of a steric structure.

(6) ELISA Sensitivity

Each 100 μl of monoclonal antibodies ANOC7-01–ANOC 707 diluted with PBS to a concentration of 10 μg/ml was poured into each well of a 96-well microplate and left overnight. The wells were blocked with 1% skim milk. 100 μl of a standard TNF-α was added to each well and incubated at 4° C. overnight. After washing the plate, 100 μl of a 1,000-fold solution of a rabbit polyclonal antibody (OCT701) against TNF-α was added and incubated for 2 hours at room temperature. The plate was washed and 100 μl of (goat) POD-labeled anti-rabbit IgG was added to each well. After incubation for 2 hours at room temperature, the plate was washed and the enzymatic activity of POD was measured.

The ELISA sensitivity of a monoclonal antibody is expressed by the TNF-α concentration of the antibody, the difference of which $OD_{492}$ adsorption and the $OD_{492}$ adsorption without TNF-α is 0.1.

The results are shown in Table 6.

TABLE 6

| Antibody No. | ELISA Sensitivity ($OD_{492}$ = 0.1) |
|---|---|
| ANOC701 | N.T. |
| ANOC702 | 1.0 ng/ml (0.10 ng/well) |
| ANOC703 | N.T. |
| ANOC704 | 1.2 ng/ml (0.12 ng/well) |
| ANOC705 | 0.44 ng/ml (0.044 ng/well) |
| ANOC706 | 0.86 ng/ml (0.086 ng/well) |
| ANOC707 | 1.0 ng/ml (0.10 ng/well) |

(8) Standard Curve by ELISA Method

100 μl of monoclonal antibody ANOC705 diluted with PBS to a concentration of 10 μg/ml was poured into each well of a 96-well microplate and left overnight at 4° C. Wells were blocked with 1% skim milk. 100 μl of a standard TNF-α was added in triplicate to each well and incubated at 4° C. overnight. After washing the plate, 100 μl of a 1,000-fold solution of a rabbit polyclonal antibody (OCT701) against TNF-α was added and incubated for 2 hours at room temperature. The plate was washed and 100 μl of (goat) POD-labeled anti-rabbit IgG was added to each well. After incubation for 2 hours at room temperature, the plate was washed and the enzymatic activity as $OD_{492}$ adsorbance was measured using o-phenylenedimine as a substrate.

The results are shown in Table 7.

TABLE 7

| TNF-α concentration (pg/ml) | 0 | 9.375 | 37.50 | 150.0 | 600.0 |
|---|---|---|---|---|---|
| Adsorbance 1 | 89 | 117 | 205 | 535 | 1510 |
| Adsorbance 2 | 95 | 123 | 206 | 540 | 1481 |
| Adsorbance 3 | 95 | 124 | 209 | 514 | 1487 |
| Mean | 93 | 121 | 207 | 530 | 1490 |
| Mean - Blank | 0 | 28 | 114 | 437 | 1397 |
| C. V. (%) | 3.7 | 3.1 | 1.0 | 2.6 | 0.7 |

Obviously, numerous modifications and variations of the present invention are possible in light of the above teachings. It is therefore to be understood that within the scope of the appended claims, the invention may be practiced otherwise than as specifically described herein.

What is claimed is:

1. Hybridoma KOCO 705 having Fermentation Research Institute Deposit No. FERM BP-2569, which produces monoclonal antibody ANOC 705, wherein said monoclonal antibody:
   (1) is an $IgG_1$ of a molecular weight of about 155 Kilo-daltons, which comprises a heavy chain having a molecular weight of about 53 Kilo-daltons and a light chain having a molecular weight of about 24.5 Kilo-daltons;
   (2) specifically reacts with SDS-denatured human tumor necrosis factor alpha; and
   (3) has neutralizing activity against human tumor necrosis factor alpha in a human tumor necrosis factor alpha bioassay.

2. Monoclonal antibody ANOC 705 secreted by hybridoma KOCO 705 having Fermentation Research Institute Deposit No. FERM BP-2569, wherein said monoclonal antibody:
   (1) is an $IgG_1$ of a molecular weight of about 155 Kilo-daltons, comprising a heavy chain having a molecular weight of about 53 Kilo-daltons and a light chain having a molecular weight of about 24.5 Kilo-daltons;
   (2) specifically reacts with SDS-denatured human tumor necrosis factor alpha; and
   (3) has neutralizing activity against human tumor necrosis factor alpha in a human tumor necrosis factor alpha bioassay.

3. A method for detecting human tumor necrosis factor alpha in a sample by an antigen-antibody binding reaction comprising the steps of:
   (A) exposing a sample to monoclonal antibody ANOC 705 secreted by hybridoma KOCO 705 having Fermentation Research Institute Deposit No. FERM BP-2569, wherein said monoclonal antibody:
   (1) is an $IgG_1$ of a molecular weight of about 155 Kilo-daltons, which comprises a heavy chain having a molecular weight of about 53 Kilo-daltons and a light chain having a molecular weight of about 24.5 Kilo-daltons;
   (2) specifically reacts with SDS-denatured human tumor necrosis factor alpha;
   (3) has neutralizing activity against human tumor necrosis factor alpha in a human tumor necrosis factor alpha bioassay; and
   (B) detecting the presence of human tumor necrosis factor in said sample by determining whether said monoclonal antibody ANOC 705 has bound to antigen.

* * * * *